US006656517B2

(12) United States Patent
Michal et al.

(10) Patent No.: US 6,656,517 B2
(45) Date of Patent: *Dec. 2, 2003

(54) THERAPEUTIC, DIAGNOSTIC, OR HYDROPHILIC COATING FOR AN INTRACORPOREAL MEDICAL DEVICE

(75) Inventors: Eugene T. Michal, San Francisco, CA (US); Christopher J. Buchko, San Francisco, CA (US); Stephen J. Bigus, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 14 days.

This patent is subject to a terminal disclaimer.

(21) Appl. No.: 09/915,413

(22) Filed: Jul. 25, 2001

(65) Prior Publication Data
US 2002/0002353 A1 Jan. 3, 2002

Related U.S. Application Data

(60) Division of application No. 09/240,914, filed on Jan. 29, 1999, now Pat. No. 6,287,285, which is a continuation-in-part of application No. 09/016,694, filed on Jan. 30, 1998, now Pat. No. 6,221,425.

(51) Int. Cl.$^7$ .............. B05D 1/00; A61L 27/00
(52) U.S. Cl. .......... 427/2.24; 427/2.25; 427/2.26; 427/2.28; 427/2.3; 427/487; 427/508; 427/372.2; 427/402; 427/407.1; 427/409; 427/414; 427/415
(58) Field of Search ............... 427/2.24, 2.25, 427/2.26, 2.28, 2.3, 487, 508, 372.2, 402, 407.1, 409, 414, 415

(56) References Cited

U.S. PATENT DOCUMENTS

| 3,695,921 A | 10/1972 | Shepherd | 117/72 |
| 3,886,947 A | 6/1975 | Sawyer | 128/348 |
| 3,895,169 A | 7/1975 | Wichterle | 428/420 |
| 4,055,682 A | 10/1977 | Merrill | 427/2 |
| 4,100,309 A | 7/1978 | Micklus et al. | 427/2 |

(List continued on next page.)

FOREIGN PATENT DOCUMENTS

| EP | 389 632 | 10/1990 |
| EP | 521 605 | 1/1993 |
| EP | 728 487 | 8/1996 |
| GB | 2 064 556 | 6/1981 |
| GB | 2 190 387 | 11/1997 |
| WO | WO 93/11751 | 6/1993 |
| WO | WO 94/26336 | 11/1994 |

Primary Examiner—Shrive P. Beck
Assistant Examiner—Jennifer Kolb Michener
(74) Attorney, Agent, or Firm—Fulwider Patton Lee & Utecht, LLP

(57) ABSTRACT

A method of providing a therapeutic, diagnostic or lubricious hydrophilic coating on an intracorporeal medical device and the coated device produced thereby, wherein the coating is durable. In one embodiment, the coating comprises a polymerized base coat and a therapeutic, diagnostic or hydrophilic top coat, where the base coat has a binding component which binds to the top coat, and a grafting component which binds to the binding component and adheres to the device. In another embodiment, the coating comprises a blend of a hydrophilic compound, a grafting component, and salt, wherein the polymerized grafting component contains uncrosslinked domains. The coating of the invention may be applied to a medical device with a polymeric surface such as a polymeric catheter, or a metal device coated with a polymeric primer or without a primer, or to a stent.

17 Claims, 4 Drawing Sheets

U.S. PATENT DOCUMENTS

| | | | |
|---|---|---|---|
| 4,111,922 A | 9/1978 | Beede et al. | 526/292 |
| 4,212,901 A | 7/1980 | van Neerbos et al. | 427/53.1 |
| 4,373,009 A | 2/1983 | Winn | 428/424.2 |
| 4,459,326 A | 7/1984 | Colombo et al. | 427/140 |
| RE31,712 E | 10/1984 | Giese | |
| 4,521,564 A | 6/1985 | Solomon et al. | 525/54.1 |
| 4,664,658 A | 5/1987 | Sawanda et al. | 604/266 |
| 4,666,437 A | 5/1987 | Lambert | 604/265 |
| 4,714,739 A | 12/1987 | Arkles | 525/92 |
| 4,722,906 A | 2/1988 | Guire | 436/501 |
| 4,729,914 A | 3/1988 | Kliment et al. | 428/36 |
| 4,876,126 A | 10/1989 | Takemura et al. | 428/35.7 |
| 4,906,237 A | 3/1990 | Johansson et al. | 604/265 |
| 4,973,493 A | 11/1990 | Guire | 427/2 |
| 4,979,959 A | 12/1990 | Guire | 623/66 |
| 5,002,582 A | 3/1991 | Guire et al. | 623/66 |
| 5,023,114 A | 6/1991 | Halpern et al. | 427/338 |
| 5,026,607 A | 6/1991 | Kiezulas | 428/423.7 |
| 5,037,677 A | 8/1991 | Halpern et al. | 427/338 |
| 5,041,100 A | 8/1991 | Rowland et al. | 604/265 |
| 5,079,093 A | 1/1992 | Akashi et al. | 428/411.1 |
| 5,091,205 A | 2/1992 | Fan | 427/2 |
| 5,094,876 A * | 3/1992 | Goldberg et al. | 428/481 |
| 5,100,689 A | 3/1992 | Goldberg et al. | 427/2 |
| 5,102,420 A | 4/1992 | Hunter et al. | 606/231 |
| 5,118,779 A * | 6/1992 | Szycher | 528/75 |
| 5,135,516 A | 8/1992 | Sahatjian et al. | 604/265 |
| 5,167,960 A | 12/1992 | Ito et al. | 424/423 |
| 5,272,012 A * | 12/1993 | Opolski | 428/423.1 |
| 5,290,548 A | 3/1994 | Goldberg et al. | 424/78.18 |
| 5,295,978 A | 3/1994 | Fan et al. | 604/265 |
| 5,416,131 A | 5/1995 | Wolff et al. | 523/105 |
| 5,441,488 A | 8/1995 | Shimura et al. | 604/265 |
| 5,470,307 A | 11/1995 | Lindall | |
| 5,509,899 A | 4/1996 | Fan et al. | 604/96 |
| 5,603,991 A | 2/1997 | Kupiecki et al. | 417/508 |
| 5,607,475 A * | 3/1997 | Cahalan et al. | 424/423 |
| 5,670,558 A | 9/1997 | Onishi | 523/112 |
| 5,693,034 A | 12/1997 | Buscemi et al. | 604/265 |
| 5,702,754 A * | 12/1997 | Zhong | 427/2.12 |
| 5,800,412 A | 9/1998 | Zhang et al. | 604/280 |
| 5,824,049 A | 10/1998 | Ragheb et al. | 623/1 |
| 5,866,113 A * | 2/1999 | Hendriks et al. | 424/78.17 |
| 6,099,563 A | 8/2000 | Zhong | 623/1.46 |

* cited by examiner

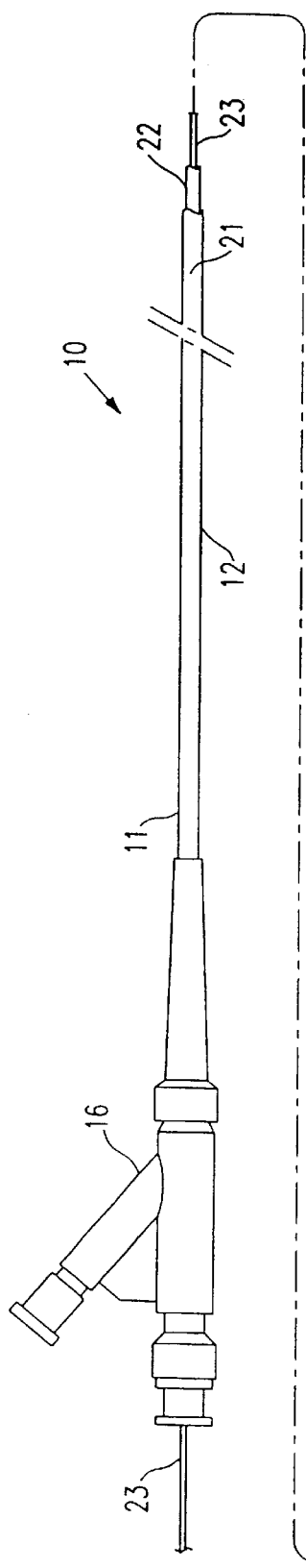
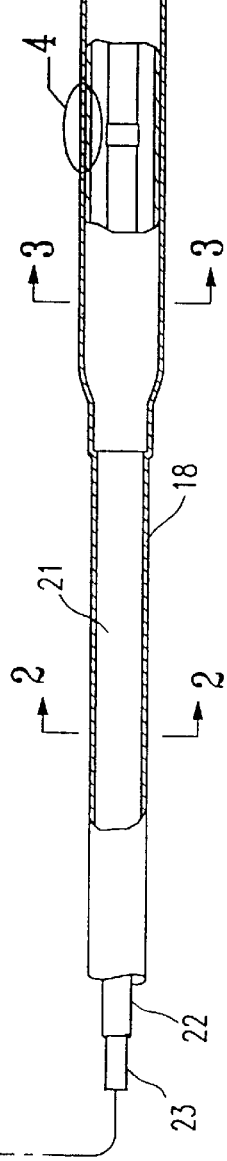
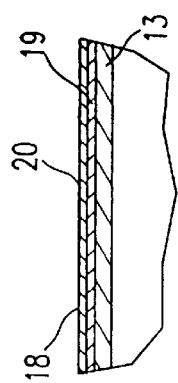
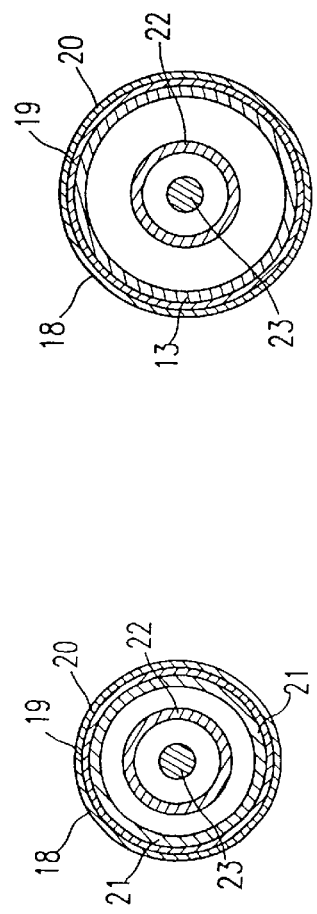
FIG. 1
FIG. 2
FIG. 3
FIG. 4

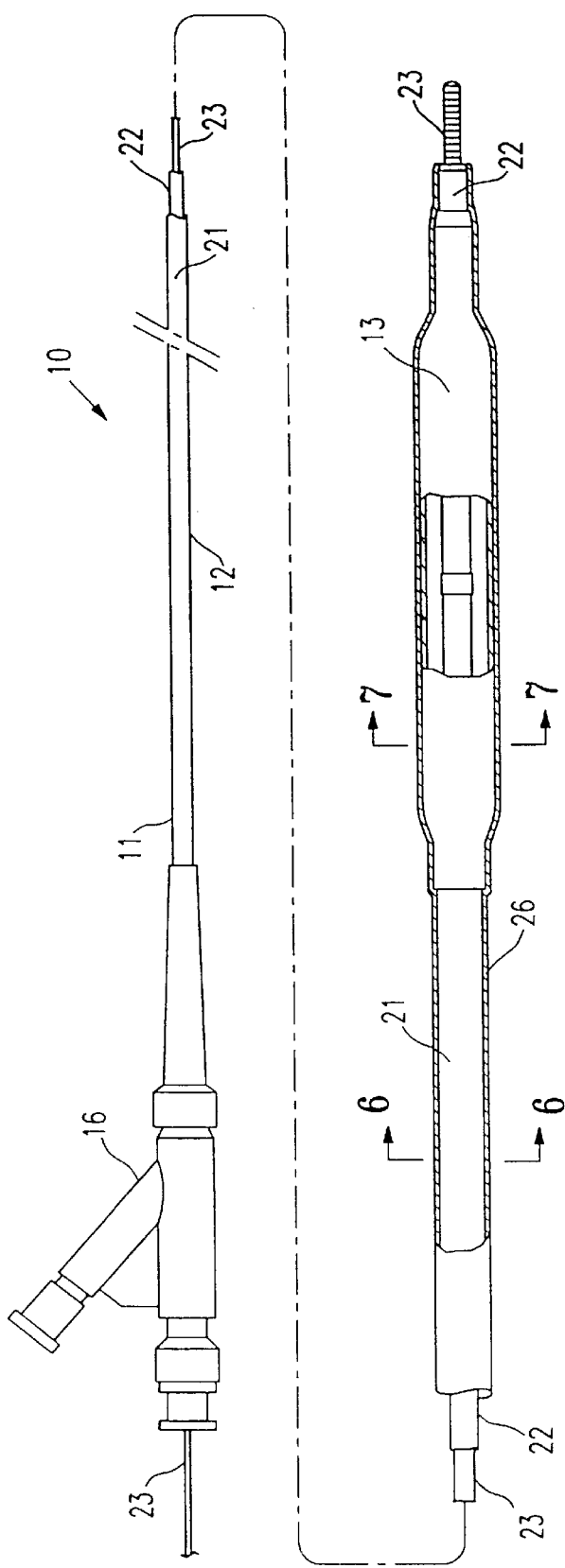
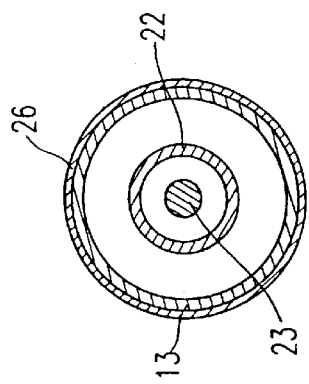
FIG. 5
FIG. 6
FIG. 7

THERAPEUTIC, DIAGNOSTIC, OR HYDROPHILIC COATING FOR AN INTRACORPOREAL MEDICAL DEVICE

This is a divisional application of prior application Ser. No. 09/240,914, filed Jan. 29, 1999, which has issued as U.S. Pat. No. 6,287,285, which in turn is a continuation-in-part of application Ser. No. 09/016,694, filed Jan. 30, 1998, which has issued as U.S. Pat. No. 6,221,425.

BACKGROUND OF THE INVENTION

This invention relates to the field of therapeutic, diagnostic, or hydrophilic coatings for intracorporeal medical devices.

The use of a medical device within a patient may be facilitated by the presence of a therapeutic, diagnostic, or hydrophilic agent on the device surface. For example, intravascular devices, such as catheters and guidewires, are more easily maneuvered within a patient's vasculature when the friction between the walls of the vessel and the intravascular device is reduced. The friction may be reduced by coating the device with a hydrophilic compound which becomes slippery after adsorbing an appreciable amount of water. Consequently, the hydrophilic coating provides lubricity when the coated device is exposed to aqueous solution, as when the coated device is exposed to water prior to insertion in the patient or to the patient's blood during use. Alternatively, coatings, such as fluoropolymers, and silicone, provide lubricity to the surface of an intracorporeal device without the need for exposure to aqueous solution. However, the degree of lubricity may vary greatly depending on the nature of the lubricious coating. Hydrophilic coatings provide superior lubricity compared to hydrophobic coatings, such as silicone, when tested against a biological tissue countersurface.

In addition to lowering the coefficient of friction of the coated device, an effective lubricious coating must strongly adhere to the device surface. The lubricious coating should remain adhered to the device surface during potentially extended periods of storage, as well as in response to abrasive forces encountered during preparation and use. Poor adhesive strength is undesirable because the lost coating may be left behind inside the patient during use, with detrimental affects and a corresponding decrease in the lubricity of the device. Typically, a trade off exists between a coating's lubricity and the coating's adhesive and cohesive strength, so that attempts to increase the adhesive strength of lubricious coatings may inadvertently decrease the lubricity of the coating. Consequently, one difficulty has been providing a highly lubricious coating that strongly adheres to a device surface.

Similarly, various medical devices, such as stents or catheters, have been coated with therapeutic or diagnostic agents, to provide localized and possibly extended exposure of the tissue to the agent. For example, drugs which prevent the proliferation of smooth muscle cells, or which promote the attachment of endothelial cells, can be coated on a stent which is then implanted at the site of a stenosis within a patient's blood vessel, to thereby inhibit restenosis following an angioplasty or stent implantation procedure. However, the agent must be strongly adhered to the device surface for effective delivery within the patient. Moreover, controlled release of the agent from the device surface within the patient may be required as part of the therapeutic or diagnostic regime.

It would be a significant advance to provide a hydrophilic coating which strongly adheres to a surface of a medical device, or a therapeutic or diagnostic coating strongly, but potentially releasably, adhered to the surface of a medical device. The present invention satisfies these and other needs.

SUMMARY OF THE INVENTION

The invention is directed to a method of providing a coating on an intracorporeal medical device, and the coated medical device produced thereby. A durable coating is provided on the medical device which modifies the device surface with a therapeutic, diagnostic, lubricious or other active agent. The coating of the invention may be used on a variety of medical devices including stents, catheters, guidewires, cardiac pacing leads, and vascular grafts.

In one embodiment, the coating on the intracorporeal medical device generally includes a base coat and a top coat. The base coat has a binding component and a grafting component, and is used to strongly adhere to the surface of the device and also to strongly bond to the top coat. Specifically, the binding component binds to both the top coat and to the grafting component, and the grafting component adheres to the device surface. The base coat containing the grafting component and binding component in a suitable carrier such as a solution is first applied to the surface of the device. The base coat is preferably polymerized, e.g., exposed to polymerizing radiation to polymerize the grafting component, and the grafting component is bonded to the binding component and adhered to the surface of the device to form a base coat on the device. The device is then coated with a top coat containing a desired therapeutic, diagnostic, or hydrophilic agent. The top coat may be applied in a solution which is allowed to evaporate, to form a top coat with a therapeutic, diagnostic, or hydrophilic agent. In another embodiment, the device is coated with a top coat comprising a linking agent, and the linking agent is exposed to the therapeutic, diagnostic, or hydrophilic agent to form a complex therewith, to thereby form the therapeutic, diagnostic or hydrophilic coating of the invention. Because the top coat bonds to the base coat, the therapeutic, diagnostic, or hydrophilic coating produced will not readily wear off.

In one embodiment, the base coat comprises a binding component which is a homofunctional compound having homofunctional groups which covalently bond to functional groups in the top coat. In a preferred embodiment, the homofunctional binding component is grafted to the grafting component by a hydrogen abstraction mechanism, in which the grafting component is activated by initiators and covalently bonds to the binding component. In another embodiment, the base coat comprises a binding component which is a heterofunctional compound having a first functional group for covalently bonding with the grafting component, and a second functional group for covalently bonding to functional groups in the top coat.

As mentioned above, the binding component of the base coat bonds to the top coat. In one embodiment, the therapeutic, diagnostic, hydrophilic or other active agent has functional groups which directly bond to functional groups of the binding component. In another embodiment, the therapeutic, diagnostic, or hydrophilic agent is bound to the binding component by a linking agent in the top coat. The linking agent may inherently have functional groups, or may be modified to include functional groups, which bond to functional groups of the binding component. The linking agent may be bound to the base coat and thereafter exposed to the therapeutic, diagnostic or hydrophilic agent, or alternatively, the linking agent may be exposed to the agent before or during the binding of the linking agent to the base coat.

A variety of suitable linking agents may be used, including avidin-biotin complexes, and functionalized liposomes and microsponges and microspheres. Avidin is a polypeptide composed of at least 128 amino acid residues. Typically however, the single polypeptide chain is a subunit associated with three essentially identical polypeptide chains, forming a tetramer. Avidin as a receptor is typically used in conjunction with its highly specific ligand, biotin, $C_{10}H_{16}N_2O_3S$. An avidin tetramer will bind 4 biotin molecules in solution in a noncovalent interaction which has a binding constant of about $10^{15}$ $M^{-1}$, a half-life in vivo of about 89 days, and which is essentially undisturbed by organic solvents. Biotinylation, or the process of covalently binding biotin to another molecule, typically takes place by N-hydroxysuccinimide binding. Spacer molecules may be inserted between the avidin and the base coat, or between the biotin and the therapeutic or diagnostic agent, as is known in the art, to facilitate avidin-biotin binding or improve the activity of the therapeutic or diagnostic agent. The avidin or the biotin molecule may be chemically altered to decrease the binding constant, to thereby tailor the dissociation rate in vivo, and provide controlled release of the therapeutic or diagnostic agent bound thereto. Avidin and biotin are available from a variety of commercial suppliers, such as Sigma. In one embodiment, avidin covalently binds to the binding component of the base coat, and binds to a biotinylated therapeutic or diagnostic agent, such as a biotinylated protein, antibody, peptide or oligonucleotide. However, the avidin-biotin linking agent may alternatively have biotin moieties covalently bound to the binding component of the base coat, and avidin moieties bound to the therapeutic or diagnostic agent. Alternatively, biotin may be covalently bound to the base coat and to the therapeutic or diagnostic agent, with avidin, by virtue of its multivalency with biotin, binding the two biotin moieties together.

Liposomes are lipid molecules formed into a typically spherically shaped arrangement defining aqueous and membranal inner compartments. Liposomes can be used to encapsulate compounds such as therapeutic and diagnostic agents within the inner compartments, and deliver such agents to desired sites within a patient. The agents contained by the liposome may be released by the liposome and incorporated into the patient's cells, as for example, by virtue of the similarity of the liposome to the lipid bilayer that makes up the cell membrane. A variety of suitable liposomes may be used, including those available from NeXstar Pharmaceuticals or Liposome, Inc, if functionalized as by the procedures described herein.

Microsponges are high surface area polymeric spheres having a network of cavities which may contain compounds such as therapeutic or diagnostic agents. The microsponges are typically synthesized by aqueous suspension polymerization using vinyl and acrylic monomers. The monomers may be mono or difunctional, so that the polymerized spheres may be cross-linked, thus providing shape stability. Process conditions and monomer selection can be varied to tailor properties such as pore volume and solvent swellability, and the microsponges may be synthesized in a controlled range of mean diameters, including small diameters of about 2 micrometers or less. A standard bead composition would be a copolymer of styrene and di-vinyl benzene (DVB). The agents contained by the polymeric microsponges may be gradually released therefrom within the patient due to mechanical or thermal stress or sonication. A variety of suitable microsponges may be used, including those available from Advanced Polymer Systems, if functionalized as by the procedures described herein.

A variety of suitable therapeutic, diagnostic or hydrophilic agents may be used. For example, the therapeutic or diagnostic agent may be selected from the group consisting of proteins; peptides; oligonucleotides; antisense oligonucleotides; cellular adhesion promoting proteins or peptides including extracellular matrix proteins; polysaccharides such as heparin, hirudin, hyaluronan, and chondrotin; nitric oxide donating compounds; growth factor such as VEGF; Taxol; Paclitaxel; Carboplatin; and Cisplaten.

The therapeutic or diagnostic agents may be used for a variety of purposes, including improving the biocompatibility of the intracorporeal medical device and inhibiting restenosis. For example, antisense oligonucleotides may be used to improve biocompatibility of the medical device, or to inhibit or prevent restenosis, where the antisense oligonucleotide inhibits cell migration, inhibits synthesis of extracellular matrix proteins or growth factors, or induces apoptosis. Suitable antisense oligonucleotides are include those described in U.S. Pat. Nos. 5,470,307, 5,593,974, and 5,756,476, and Uhlmann, E. et al, Antisense Oligonucleotides: A New Therapeutic Principle, Chemical Reviews, 90(4), 544–579 (1990), incorporated by reference in their entireties. The antisense oligonucleotides may be modified with avidin or biotin, or to contain hydrophobic groups such as cholesterol, to facilitate cellular uptake and prevent degradation by nucleases. Similarly, extracellular matrix proteins may be used to improve biocompatibility of the medical device, or inhibit or prevent restenosis. Extracellular matrix proteins, such as fibronectin, laminin, collagen, and vitronectin, or synthetic peptide analogues of extracellular matrix proteins, have an amino acid sequence which contributes to cell adhesion. Synthetic peptide analogues of extracellular matrix proteins can also be used which retain the biological function but have a lower molecular weight and different solution properties. The extracellular matrix proteins or peptides will attract migrating cells within the patient, and thus inhibit restenosis by preventing the cells from accumulating in the arterial lumen. Additionally, by attracting migrating cells, they facilitate integration with tissue of implanted devices, such as stents, and wound healing, and the uptake by cells of other therapeutic agents bound to the device surface. Additionally, the extracellular matrix proteins bound to the device surface may facilitate in vitro seeding of endothelial cells to the device prior to implantation or introduction of the device within the patient. In one embodiment, the extracellular matrix protein vitronectin is bound to the device surface, and an antibody to the B1 integrin subunit is bound to the device surface or is delivered locally or systemically. This antibody has been shown to block cellular adhesion to all extracellular matrix proteins except vitronectin, thereby enhancing the adhesive power of the modified device surface. Similarly, nitric oxide donor drugs may be used to improve biocompatibility of a medical device, and may also prevent or inhibit platelet aggregation and promote wound healing. Additionally, nitric oxide donor drugs may be used as a vasodilator relaxing smooth muscles of a vessel prior to, during, and/or after angioplasty or stent placement. A variety of suitable nitric oxide donor drugs can be used including nitric oxide-polyamine complexes, 2-methyl-2-nitrosopropane, S-Nitroso-N-acetyl-D,L-penicillamine, 3-morpholoinosydoimine, sodium nitrate, s-nitrosoglutathione, sodium nitroprusside, and nitroglycerine. The structure and mechanisms of suitable nitric oxide donor drugs are disclosed in U.S. Pat. No. 5,650,447, incorporated by reference in its entirety.

A variety of suitable hydrophilic or lubricious compounds can be used as the hydrophilic agent. The hydrophilic agent typically has functional groups which directly bond to the binding component of the base coat. Because the hydrophilic compound is bound to the base coat, it will not readily wear off even after repeated hydration and abrasion. To hydrate the hydrophilic coating on the device and render the coating highly lubricious, the coated device may be exposed to aqueous fluid either before insertion into a patient or by contact with body fluid while inside the patient.

In another embodiment, a base coat is not used, and a coating is provided on the intracorporeal medical device, which in a presently preferred embodiment is a hydrophilic coating generally including a hydrophilic polymer, an ionic compound with at least one inorganic ion, and a grafting component. The grafting component is polymerized as outlined above, so that the grafting component grafts to the device and crosslinks to the hydrophilic polymer, to form a hydrophilic coating on the device. When the coated device is hydrated, the coating absorbs water and is highly lubricious, but does not dissolve in the aqueous or blood medium because the hydrophilic polymer is immobilized by the grafted network. Moreover, the ionic compound, or salt, increases the lubricity of the hydrophilic coating by providing uncrosslinked domains in the crosslinked matrix. Because the ability of a hydrophilic polymer to absorb water is decreased when the polymer is crosslinked, the salt enhances the polymer lubricity by disrupting the crosslinking of the hydrophilic polymer into the grafting component crosslinked network. Therefore, when the hydrophilic coating is hydrated by exposure to a solvent and the salt dissolves, these uncrosslinked domains provide additional lubricity by increasing the contact between the hydrophilic polymer and the countersurface, e.g. the patient's vessel wall, and hence additional lubricity.

The coating of the invention can be applied to any device having a polymeric surface, as for example, a catheter formed of conventional materials, or a metal device, such as a metal guidewire or stent, having a polymer primer coat. For example, the catheter components may be formed of high density polyethylene, polyethylene terephthalate, and polyolephinic ionomers such as Surlyn®, nylon and the like which are frequently used to form dilatation balloons or catheter shafts. Additionally, the therapeutic, diagnostic, or hydrophilic coating of the invention can be applied directly to a metal device. For example, in the embodiment of the invention having a base coat and a top coat, the base coat adheres, as by Van der Waals forces, to the metal surface of the device, so that a polymeric primer coat need not be used.

In the embodiment of the coating of the invention having a hydrophilic agent, the coated device has a superior hydrophilic coating which is highly lubricious against biological tissue and is strongly bound to the device surface due to the grafting component used alone or in combination with the binding component. In the case of a PTCA catheter or guidewire, the coating serves to enhance device access to distal lesions and the ease with which a device crosses small diameter athlerosclerotic lesions.

In the embodiment of the coating of the invention having a therapeutic or diagnostic agent bound to the medical device surface, directly or via a linking agent, the coating of the invention provides localized delivery of the therapeutic or diagnostic agent. Similarly, the coating of the invention improves the residence time of the therapeutic or diagnostic agent. By binding the agent to the device, the rapid clearance from the bloodstream of the therapeutic agent, as for example when the body's immune system phagocytizes the therapeutic agent or a liposome containing the agent, is avoided.

These and other advantages of the invention will become more apparent from the following detailed description of the invention and the accompanying exemplary drawings.

BRIEF DESCRIPTION OF THE DRAWINGS

FIG. 1 is an elevational view, partially in section, of a dilatation catheter having a coating of the invention.

FIGS. 2 and 3 are transverse cross sections of the catheter shown in FIG. 1 taken along lines 2—2 and 3—3, respectively.

FIG. 4 is an enlarged longitudinal cross-sectional view of the coated catheter shown in FIG. 1 within the circle 4.

FIG. 5 is an elevational view, partially in section, of a dilatation catheter having a coating of the invention.

FIGS. 6 and 7 are transverse cross sections of the catheter shown in FIG. 5 taken along lines 6—6 and 7—7, respectively.

DETAILED DESCRIPTION OF THE INVENTION

Figure 8:
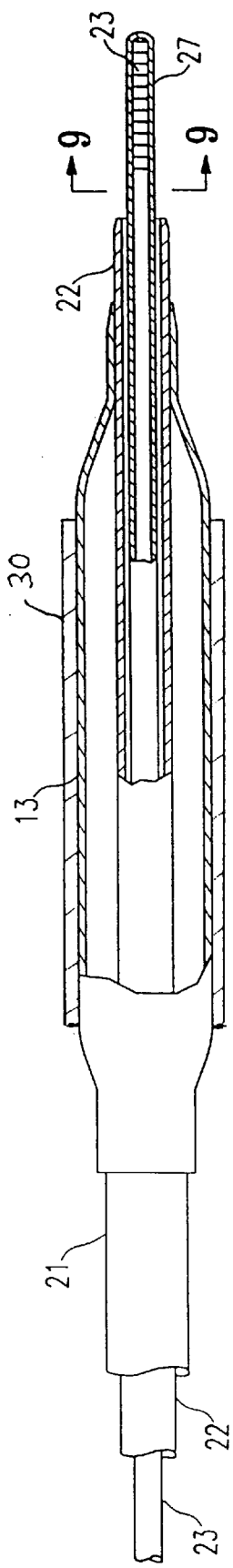
FIG. 8 is a longitudinal cross section of a guidewire having a coating of the invention.

In one embodiment of the invention, shown in FIG. 1, the intracorporeal medical device having a coating of the invention 10 is a balloon catheter 11, generally including an elongated catheter shaft 12, with an inflatable balloon 13 on the distal end and an adapter mounted 16 on the proximal end. The catheter shaft 11 and balloon 13 are provided with a coating 18 with a therapeutic, diagnostic, lubricious, or other active agent. As best shown in FIG. 4, illustrating an enlarged longitudinal cross section of the coating 18 shown in FIG. 1 within circle 4, the coating comprises a base coat 19 and a top coat 20. FIGS. 2 and 3 illustrate a transverse cross section of the catheter of FIG. 1 taken along lines 2—2 and 3—3, respectively. The catheter shaft may comprise an outer tubular member 21, and an inner tubular member 22 disposed in a lumen of the outer tubular member and having a lumen configured to slidably receive a guidewire 23.

In the embodiment illustrated in FIGS. 1–4 in which the therapeutic, diagnostic, or hydrophilic coating comprises a base coat 19 and a top coat 20, the base coat has a grafting component and a binding component. The grafting component is selected from the group consisting of vinyl compounds, acrylate compounds, and allyl compounds, such as any oligomer or monomer with one or more vinyl, acrylate or allyl double bonds. Exemplary of the vinyl compounds are di-vinyl benzene, n-vinyl pyrrolidone, and triethylene glycol divinyl ether. Exemplary of the acrylate compounds are tri-methylol propane tri-acrylate, pentaerythritol tetra-acrylate, and Bisphenol A. ethoxylate diacrylate. Exemplary of the allyl compounds are allyl ether, di-allyl maleate, and tri-allyl isocyanurate.

To form the base coat 19, the grafting component is blended with a binding component. The binding component and a compound in the top coat 20 have functional groups capable of binding to one another, so that the top coat will be securely bound to the medical device through covalent attachment to the binding component. In one embodiment, the top coat 20 comprises a therapeutic, diagnostic or hydrophilic agent which bonds to the functional groups of the binding component. In another embodiment, the top coat 20 comprises a linking agent which bonds to the binding component, and which forms a complex with a therapeutic, diagnostic or hydrophilic agent to thereby bond the agent to the medical device. In a presently preferred embodiment, the linking agent is selected from the group consisting of avidin-biotin complexes, microsponges, and liposomes. The complex of the linking agent and the therapeutic, diagnostic or hydrophilic agent may be formed by a bond between the linking and the therapeutic, diagnostic or hydrophilic agents, as in the case of an avidin-biotin linking agent. Alternatively, the complex may be formed by the encapsulation or containment of the therapeutic, diagnostic or hydrophilic agent by the linking agent, as in the case of a liposome, microsponge, or microsphere linking agent.

In a presently preferred embodiment, the binding component comprises a homodi- or homotri-functional monomer with a functional group for binding to the functional group of the top coat, or a heterodifunctional monomer with a first functional group for binding to the functional group of the top coat and a second functional group for binding to the functional group of the grafting component of the base coat. The nature of the functional groups of the binding component varies depending on the identity of the functional groups of the top coat 20 that will be applied thereto. The binding component has one or more functional groups selected from the group consisting of aziridine, carbodiimide, aldehyde, isocyanate, succinimide, maleimide, oxirane, and carboxyl derivatized with carbodiimide or tresyl or succinimide.

In one embodiment, the binding component is selected from the group consisting of polyaziridine and polycarbodiimide resin compounds, and the top coat has carboxyl groups capable of binding to the binding component. The top coat may also have an amine group in the case of a carbodiimide resin binding component. Exemplary of the polyaziridine compounds are tri-aziridine oligomer, such as Zeneca cx-100, available from Zeneca Resins. Exemplary of the carbodiimide compounds are XL-29SE available from Union Carbide. The hydrophilic agent is a polymer showing appreciable water absorption and containing carboxyl groups, including but not limited to, polyacrylic acid, alginic acid, carboxy methyl cellulose, and hyaluronic acid. The carboxy hydrophilic coating may be exposed to a basic solution, such as 0.1 N potassium or sodium hydroxide, to neutralize free carboxyl groups on the hydrophilic coating, and the coating then rinsed in water to remove the basic solution. Exemplary of the therapeutic or diagnostic agents having carboxy functional groups are proteins, peptide, antisense and sense oligonucleotides, and carboxy functional drugs.

In another embodiment, the binding component comprises an aldehyde compound and the top coat is a compound having amine groups. The binding component may be a homodi- or homotri-functional monomers having aldehyde groups, such as glutaraldehyde and acrolein. Alternatively, the binding component may be a heterodifunctional monomers having a first functional group and a second functional group, the first functional group being aldehyde groups, and the second functional group being groups such as vinyl groups. Exemplary of such heterodifunctional compounds are cinnamaldehyde. Exemplary of the hydrophilic agent are a (co)monomer selected from the group consisting of 2-aminoethyl acrylate, 2-aminoethyl methacrylate, and N-(3-aminopropyl) methacrylamide; or a polymer of at least one of said (co)monomers co-polymerized with hydrophilic monomers selected from the group consisting of acrylamide, di-methyl acrylamide, and N-vinyl pyrrolidone; or a peptide having a secondary basic group for reaction with the aldehyde of the binding component, such as arginine, glutamine, and histidine, which include but are not limited to gelatin, hirudin, and albumin; or polyethylenimine. Exemplary of the therapeutic or diagnostic agents having amine groups are peptides, proteins, nitric oxide donating compounds, antisense and sense oligonucleotides.

In another embodiment, the binding component is an isocyanate compound and the top coat is a compound containing hydroxy or amine groups. The binding component may be a homodi- or homotri-functional monomers having isocyanate groups. Exemplary of such isocyanate compounds are an isocyanate of hexamethylene diisocyanate, such as Desmodur 3300 available from Bayer, an aliphatic or aromatic isocyanate monomer, biuret or isocyanurate oligomer, or polyol or polyamine chain extended variant of such starting materials as 1,6 hexamethylene diisocyanate, isophorone diisocyanate, toluene diisocyanate, diphenylmethane-diisocyanate, bis(4-isocyanato cyclohexyl) methane. The isocyanate compound can also be the monomer or polymer made from allyl isocyanate or other such monomers. Alternatively, the binding component may be a heterodifunctional monomers, the first functional group being isocyanate groups, and the second functional group being groups such as methacrylate. Exemplary of such isocyanate compounds are isocyanato-ethylmethacrylate. Exemplary of the hydrophilic agent are poly(vinyl alcohol), hydroxy propyl cellulose, hyaluronic acid, a peptide having a secondary basic group for reaction with the isocyanate of the binding component, and a copolymer blend of a first monomer selected from the group consisting of vinyl and acrylic monomers and a second monomer selected from the group consisting of hydroxy and amine monomers. Examples of the peptide include but are not limited to gelatin, hirudin, and albumin, and examples of the copolymer blend hydrophilic polymers include but are not limited to an 80/20 mixture of acrylamide and hydroxy ethyl methacrylate. Exemplary of the therapeutic or diagnostic agents having amine or hydroxyl groups are peptides, proteins, nitric oxide donating compounds, antisense and sense oligonucleotides.

In another embodiment, the binding component is a succinimide or oxirane compound and the top coat is a compound containing amine groups. The binding component may be a heterodifunctional monomers, the first functional group being succinimide or oxirane groups, and the second functional group being groups such as acrylate, methacrylate, and allyl. Examples of such compounds include N-acryloxysuccinimide, having a succinimide first group and an acrylate second group (C=CHCOOR), glycidyl methacrylate having an oxirane first group and a methacrylate second group (C=CCH$_3$COOR), and allyl glycidyl ether having an oxirane first group and an allyl second group (H$_2$C=CHCH$_2$). The top coat compounds having amine groups are as given above.

In another embodiment the binding component is a heterodifunctional monomers, the first functional group being maleimide groups, and the second functional group being groups such as vinyl (H$_2$C=CH). Examples of such compounds include N-(4-vinylphenyl)maleimide. The top coat compounds have thiol (SH) groups. Exemplary of such top coat compounds are peptides, proteins, nitric oxide donating compounds, antisense and sense oligonucleotides.

In another embodiment the binding component contains carboxy groups that have been derivatized. For example, a binding compound having carboxy groups can be derivatized by carbodiimide or tresyl (i.e., trifluoroethane sulfonyl) or succinimide functional compounds to provide a binding component that will covalently bind to amine groups in the top coat. Examples of derivatizing agents include 1-ethyl-3-(3-dimethylaminopropyl carbodiimide) (i.e., EDAC), and tresyl chloride. Examples of suitable carboxy containing compounds include acrylic acid, methacrylic acid, itaconic acid, ethylene acrylic acid (such as Primacor, available from Dow). The carboxy binding compounds would be applied to the medical device surface as part of a base coat as described herein, and cured. The carboxy containing compounds could be radiation or otherwise cured, except in the case of ethylene acrylic acid binding compounds where the compound is deposited on the device by a solvent solution or neutralized aqueous dispersion and cured by thermal drying to remove the solvent. Thereafter, the carboxy compounds are derivatized, as by immersing the cured base coat in a solution of the derivatizing agent, and rinsing the surface after the derivatizing reaction to remove excess agent, to form a base coat having a binding component having a functional group of carboxy that had been derivatized with carbodiimide or tresyl or succinimide. Thereafter, the derivatized surface may be immersed into a solution of the top coat having an amine functional group.

In one embodiment of the linking agent, the linking agent inherently has the functional groups outlined above for binding to the functional groups of the binding component of the base coat. For example, amine, carboxy, or hydroxy functional groups on the avidin moiety of an avidin-biotin linking agent can bind the avidin-biotin linking agent to the base coat. Additionally, where the biotin moiety of the avidin-biotin linking agent binds to the base coat, n-hydroxy succinimide ester of the biotin moiety can be used to bind the biotin to an amine or amine functionalized surface of the base coat. An amine functionalized surface can be obtain by using a monomer such as n-(3-aminopropyl) methacrylamide hydrochloride in the base coat. Alternatively, biotin can be bound to carboxyl groups on a drug or carboxyl functional surface by using biotin hydrazide per well established methods.

Alternatively, the linking agent may be modified to include the functional groups. Primary amine groups, hydroxyl, thiol, or carboxy groups can be added to liposome or microsponge linking agents to permit covalent attachment of the linking agent to the base coat functional groups. For example, compounds having the desired functional groups, such as monomers such as hydroxyethylmethacrylate having a hydroxy functional group and n-(3-aminopropyl) methacylamide having an amine functional group, can be introduced into the bead composition during synthesis of the microsponges to form the functionalized microsponges. Functionalized microsponges can be made by the methods disclosed in U.S. Pat. No. 5,840,293. Typically, hydrophilic monomers will be used to functionalize the microsponges used in the coating of the invention. The process used for functionalizing the microsponges with hydrophilic monomers such as hydroxyethyl methacrylate, n-(3-aminopropyl) methacrylamide hydrochloride, and acrylic acid, is inverse suspension polymerization. However, when hydrophobic monomers are used, a suspension polymerization process is used. Liposomes can be functionalized by using phosphatidyl serine (di-fatty acid) or phosphatidyl ethanolamine (di-fatty acid) or a mixture of the two as the feedstock. Fatty acids can be oleic, palmitic or others. These materials will provide primary functionality, permitting binding to a basecoat containing isocyanate or aldehyde functionality. Alternatively, a carboxylated surface can be derivitized using a carbodiimide such as EDC, and this can be used to bind the functionalized liposomes.

Additionally, two different linking agents may be used to bind the therapeutic, diagnostic or hydrophilic agent to the base coat. For example, avidin-biotin may be bound to the binding component of the base coat and also to a second linking agent such as a functionalized liposome or microsponge which encapsulates a therapeutic or diagnostic agent.

In the embodiment illustrated in FIGS. 1–4, in which the coating 18 comprises a top coat 20 on a base coat 19 having a binding and a grafting component, the method of providing a therapeutic, diagnostic or lubricious hydrophilic coating on an intracorporeal medical device of the invention comprises, applying to the medical device a solution having a binding component and a grafting component, and polymerizing the grafting component so that the grafting component grafts to the device and crosslinks with, or otherwise binds as by copolymerization or covalent bonding to, the binding component, to form the base coat 19. The device thus coated with the base coat 19, hereafter the base coated device, may typically be dried, either a room temperature or at elevated temperatures, to evaporate the base coat solution solvent, before polymerizing the grafting component. The base coat on the device is then coated with a solution of the top coat agent (i.e., the therapeutic, diagnostic or hydrophilic agent, or the linking agent) to form the top coat 20. The coated device is then dried at elevated or room temperature. The top coat agent grafts via covalent bonds to the binding component, to form the coating 18 on the device. In the case of a hydrophilic agent, the coating 18 can then be hydrated by exposure to aqueous solution, rendering it highly lubricious.

In the embodiment having a linking agent, the solution of the top coat applied to the base coat comprises a linking agent that is already exposed to the therapeutic, diagnostic or hydrophilic agent or that will subsequently be exposed to the agent. The microsponge linking agents are bound to the binding component and thereafter exposed to a solution of the therapeutic, diagnostic or hydrophilic agent, to introduce the agent into the pores of the microsponge. Alternatively, the microsponge linking agent may be preloaded with the therapeutic, diagnostic or hydrophilic agent before or during bonding to the base coat. The microsponges may be exposed to the therapeutic or diagnostic agent as, for example, by immersing the microsponges into a solution of the agent before or after the microsponges are attached to the base coat, and thereafter evaporating the solvent. The avidin-biotin and liposome linking agents are typically exposed to the therapeutic, diagnostic or hydrophilic agent before being bonded to the base coat.

Polymerization of the grafting component is carried out by irradiating the base coated device with ultra-violet (UV) light or with electron beam irradiation. When UV light is used, photoinitiators must be present in the base coat solution. In the process of polymerization, the UV light induces free radicals on the photoinitiators, which transfer to the acrylate, vinyl or allyl compound of the grafting component, thereby causing the grafting component to polymerize into a crosslinked network. These processes, involving UV or electron beam irradiation, are known in the art as radiation induced acrylate/vinyl free radical polymerization. Additionally, during this process, the acrylate, vinyl or allyl network crosslinks, or otherwise binds as by copolymerization or covalent bonding, to the functional groups of the binding component, e.g. the polyaziridine or polycarbodiimide oligomers, the isocyanate containing oligomer, or the aldehyde or polyaldehyde compound, and grafts to the device polymeric surface via a hydrogen abstraction mechanism. The result is a well adhered base coat 19 containing free unreacted binding component functional groups on the surface of the coating available to graft the agent of the top coat 20.

The photoinitiator is any compound that generates a free radical when irradiated with UV or visible light. Exemplary of the photoinitiator are benzophenone, benzoin methyl ether, 2,2 dimethoxy-2-phenylacetophenone, 1-hydroxycyclohexyl phenyl ketone, and ethyl 4-(dimethylamino)benzoate.

FIG. 5 illustrates another embodiment of the invention, in which the binding component is omitted, and the coating 26 comprises a grafting component blended with the hydrophilic agent before being applied to the device. FIGS. 6 and 7 illustrate transverse cross sections of the coated catheter shown in FIG. 5. In this embodiment of the invention, the method of providing a lubricious hydrophilic coating on an intracorporeal medical device comprises applying to the device a solution comprising a hydrophilic polymer, an ionic compound with at least one inorganic ion, and a grafting component. The grafting component is polymerized so that the grafting component grafts to the device and crosslinks with the hydrophilic polymer, with some uncrosslinked domains remaining in the crosslinked matrix. The coated device is typically dried before exposure to the polymerizing radiation. The coated device can then be hydrated by exposure to an aqueous solution, whereby the hydrophilic polymer absorbs the solution and the salt dissolves, rendering the coating highly lubricious.

In the embodiment illustrated in FIG. 5 the hydrophilic agent is any polymer displaying appreciable water absorption, including but not limited to poly(ethylene oxide), poly(vinylpyrrolidone), poly(vinyl alcohol), poly(acrylamide), alginic acid, hyaluronic acid, poly(acrylic acid), and guar gum. The grafting component and its polymerization are as discussed in the previous embodiments. Suitable ionic compounds with at least 1 inorganic ion, i.e. a salt, include but are not limited to potassium bromide, and sodium chloride.

Figure 9:
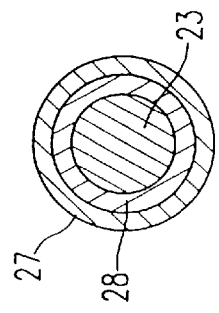
FIG. 9 is a transverse cross section of the guidewire shown in FIG. 8 taken along lines 8—8.

In another aspect of the invention in which the medical device is formed of metal, a primer coating is applied to the device before applying the therapeutic, diagnostic or hydrophilic coating. FIG. 8 illustrates a metal guidewire 23 having a primer coat 28 and a therapeutic, diagnostic or lubricious, hydrophilic coating 27 of the invention. The primer coat 28 is applied to at least the entire length of the guidewire to be coated with the therapeutic, diagnostic or hydrophilic coating. The polymerized primer coating 28 is selected from the group consisting of vinyl, acrylate and allyl compounds. The vinyl or acrylate compounds of the primer and the polymerization of these compounds are as discussed above for the grafting components. FIG. 9 illustrates a transverse cross section of the guidewire shown in FIG. 8 along lines 9—9. In the presently preferred embodiment illustrated in FIG. 8, the coating 27 is a hydrophilic coating which is the same as coating 26, comprising a grafting component blended directly with a hydrophilic agent and an ionic compound with at least one inorganic ion. In the method of the invention, a solution comprising the primer coating is applied to the guidewire 23, and primer coat 28 is typically dried before the vinyl or acrylate compound is polymerized.

A solution comprising the hydrophilic agent and grafting component is then applied to the primer coat and exposed to polymerizing radiation, to form the hydrophilic coating 27 on the guidewire. However, the coating 27 may comprise the therapeutic, diagnostic or hydrophilic coating 18 having a base coat 19 and top coat 20 as discussed above, and, in which case, the primer coat 28 may be omitted.

Figure 10:
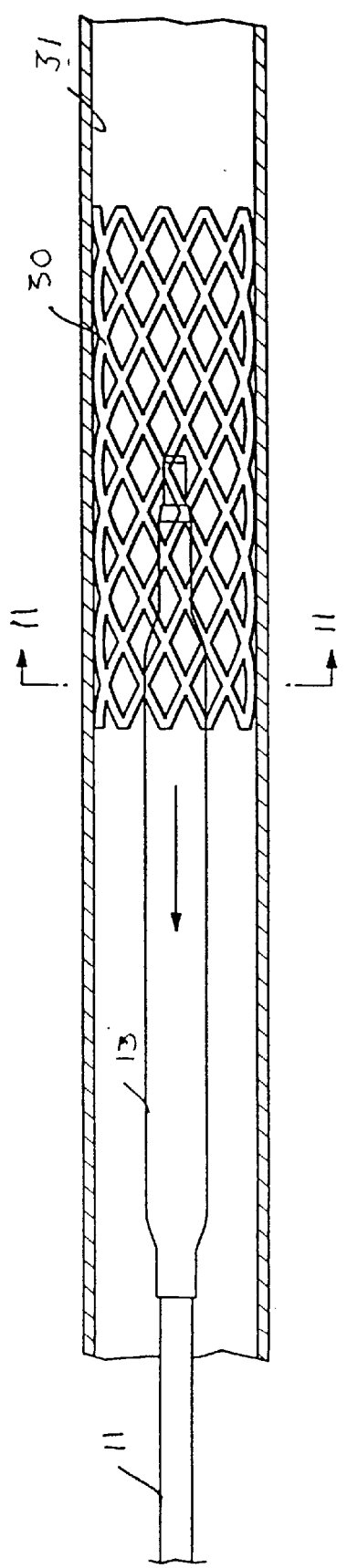
FIG. 10 is an elevational view of a stent having a coating of the invention, with a balloon catheter, within a body lumen.
Figure 12:
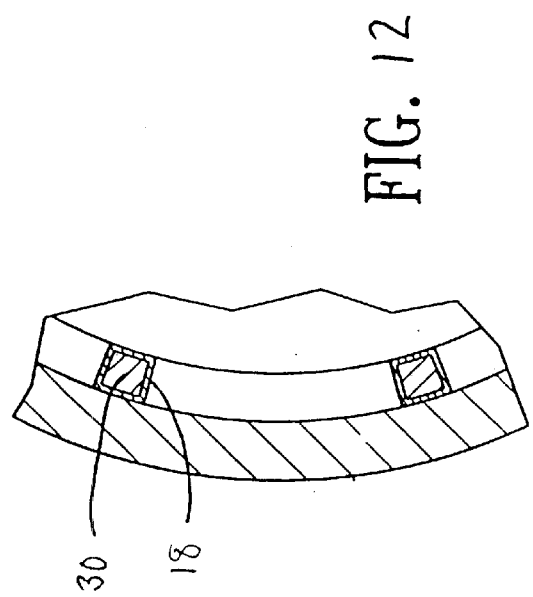
FIG. 12 is an enlarged view of the stent shown in FIG. 11 within the circle 12, illustrating the coating on the stent.
Figure 11:
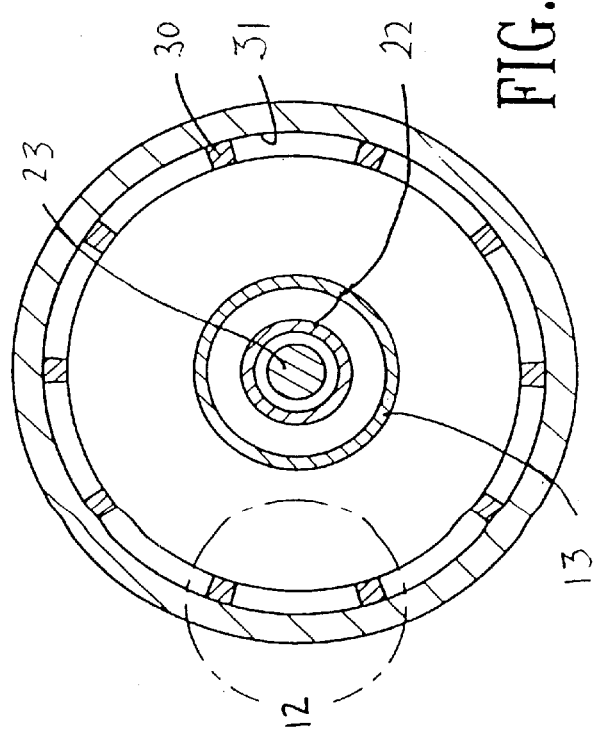
FIG. 11 is a transverse cross sectional view of the stent and catheter shown in FIG. 10, taken along lines 11—11.

In another embodiment of the invention, illustrated in FIGS. 8 and 10–12, the therapeutic, diagnostic, or hydrophilic coating of the invention is applied to a prosthesis, such as an intravascular stent. FIG. 8 illustrates a stent 30 on a balloon 13 of a balloon catheter 11 for introduction into a patient's vasculature. FIG. 10 illustrates the stent after being implanted within the patient's vessel 31. Typically, the stent is expanded within the patients vessel 31 by inflation of the balloon 13, the balloon deflated and the balloon catheter withdrawn, leaving the stent implanted in the vessel. FIG. 11 illustrates a transverse cross sectional view of the stent, and catheter, shown in FIG. 10, taken along lines 11—11. The stent is coated with a diagnostic, therapeutic, or hydrophilic coating of the invention, as illustrated in more detail in FIG. 12, showing an enlarged view of the stent shown in FIG. 11, within circle 12. In a presently preferred embodiment, the stent is coated with a therapeutic coating of the invention, such as a therapeutic agent to inhibit or prevent restenosis, using the coating 18 comprising base coat 19 and top coat 20. In a presently preferred embodiment, the restenosis therapeutic agent is a peptide or protein, or a nitric oxide donating compound.

In one embodiment of the invention, release of the therapeutic or diagnostic agent within the patient from the medical device surface is provided by the coating of the invention. Such release of the therapeutic agent from the device surface may be desirable as when the agent is effective when taken up by cells within the patient over a desired period of time. For example, an antisense oligonucleotide may be bound to the base coat by binding the antisense oligonucleotide to a sense oligonucleotide via Watson-Crick base-pairing. However, when the complementarity of the sense sequence is varied, the dissociation constant of the base-pair bond may be controlled, to thereby control the release of the antisense oligonucleotide from the device surface. Similarly, the avidin or biotin moiety of an avidin-biotin linking agent may be chemically altered to decrease the binding constant and thereby tailor the in vivo half life of the avidin-biotin complex. Additionally, linking agents such as liposomes and microsponges can be acted upon, as by application of mechanical or thermal stress, to cause them to release the therapeutic agents contained thereby. Microcapsules, such as microsponges bound to the surface of a medical device may be exposed to ultrasound which results in release of the therapeutic agent contained within the pores of the microsponges. In the case of a stent or other implanted medical device, the ultrasound may be applied noninvasively upon a return trip to the doctor so that the release of the therapeutic agent from the stent may occur at a desired time, which may be days, weeks, or months after the coated stent is implanted in the patient.

As discussed above, a variety of suitable therapeutic, diagnostic or hydrophilic agents may be used, and in some embodiments, a linking agent may be used to bind the therapeutic, diagnostic, or hydrophilic agent to the base coat. The use of a linking agent and the type of linking agent used depends on the nature of the therapeutic, diagnostic or hydrophilic agent. Those therapeutic agents which have the functional groups outlined above may be directly attached to the surface and/or may be attached by a linking agent. For example, proteins, peptides, antisense oligonucleotides, extracellular matrix proteins, and nitric oxide donating compounds have amine groups and hydroxyl functional groups which bind to isocyanate or aldehyde of the binding component, to bind the agent directly to base coat. Linking agents such as microsponges, liposomes and biotin-avidin complexes must be used for binding the agents which do not have the functional groups, and they may be used for binding the agents which do have the required functional groups. For example, any of the above listed therapeutic agents in addition to VEGF, Taxol, Paclitaxel, Carboplatin, and Cisplaten may be contained in a liposome or microsponge linking agent. Similarly, peptides, proteins, antibodies, and oligonucleotides have amine and carboxyl functional groups which bind to biotin of an avidin-biotin linking agent.

The presently preferred method of coating the device with the coating(s) is by dip coating at a given rate. However, the device may be coated by numerous suitable methods, including but not limited to, spray coating, wipe coating, or other techniques known in the art. Many suitable solvents may be used in the coating solutions including but not limited to water, alcohols, and ketones.

In the presently preferred embodiments, the device is a polymeric catheter, or a metal guidewire coated with a primer or without a primer, having a hydrophilic coating of the invention, or the device is a metal device such as a stent coated with a therapeutic or diagnostic coating of the invention. However, the device can be any intracorporeal medical device in which modification of surface properties, such as by addition of a therapeutic or diagnostic agent, or by a reduction of friction or modification of the surface absorption properties, is desired. The surface of the device is generally cleaned before coating with the primer or the hydrophilic coating solutions, and may optionally be plasma treated to improve coating adhesion.

The therapeutic, diagnostic, or hydrophilic coating may be applied to all or part of the medical device. In the embodiments illustrated in FIGS. 1 and 5, the coating is on both the catheter shaft and the catheter balloon. In a presently preferred embodiment of the hydrophilic coating of the invention, the lubricious hydrophilic coating 18, 26 on a dilatation catheter covers the outer surfaces of both the catheter shaft and balloon, as illustrated in FIGS. 1 and 5. However, the hydrophilic coating may be applied to various catheter surfaces, including an inner surface of the catheter to facilitate displacement of objects, such as a guidewire, within a lumen of the catheter, or an outer surface of the inner tubular member 22. Also, the hydrophilic coating 18, 26, 27 may be applied to less than the entire outer surface of the device, as when a proximal portion of the catheter or guidewire is left uncoated to provide a handling location, or when the balloon is left uncoated to provide frictional engagement with the patient when the balloon is inflated. For example, in a typical balloon angioplasty catheter of 144 cm, the coating 18, 26 would be applied to about 2 cm to about 105 cm of the catheter. When the device is a guidewire, the coating 27 would be applied to about 2 cm to about 40 cm of the total guidewire length of 175 cm.

The following examples more specifically illustrate the invention. The percent values for the coating components is a percent by weight of the total formula weight.

EXAMPLE 1

Formula for Therapeutic, Diagnostic, or Hydrophilic Coatings Having a Base Coat and a Top Coat

| Therapeutic, Diagnostic, or Hydrophilic Coating Formula I: | | | |
|---|---|---|---|
| Coating Layer | Component | % of Non-Volatile | % of Total Formula |
| Base coat | 1. Binding component: polyaziridine or polycarbodiimide compound | 5–70% | |
| | 2. Grafting component: vinyl or acrylic functional monomer/oligomer | 10–95% | |
| | 3. Photoinitiators | 0.05–10% | |
| | 4. Solvents | N/A | 40–99% |
| Top coat | 1. Therapeutic, diagnostic, or hydrophilic agent: carboxyl containing compound | | 0.05–15% |
| | 2. Solvents | | 84–99.5% |
| | 3. Amine or base | | 0–5% |

| Therapeutic, Diagnostic, or Hydrophilic Coating Formula II: | | | |
|---|---|---|---|
| Coating Layer | Component | % of Non-Volatile | % of Total Formula |
| Base coat | 1. Binding component: isocyanate functional monomer/oligomer/polymer | 5–90% | |
| | 2. Grafting component: vinyl or acrylic functional monomer/oligomer | 5–95% | |
| | 3. Isocyanate catalyst | 0–2% | |
| | 4. Photoinitiators | 0.05–10% | |
| | 5. Solvents | N/A | 40–99% |

-continued

Therapeutic, Diagnostic, or Hydrophilic Coating Formula II:

| Coating Layer | Component | % of Non-Volatile | % of Total Formula |
|---|---|---|---|
| Top coat | 1. Therapeutic, diagnostic, or hydrophilic agent: hydroxy or amine containing compound. | | 0.05–20% |
| | 2. Solvents | | 80–99.5% |

Therapeutic, Diagnostic, or Hydrophilic Coating Formula III:

| Coating Layer | Component | % of Non-Volatile | % of Total Formula |
|---|---|---|---|
| Base coat | 1. Binding component: aldehyde compound | 5–90% | |
| | 2. Grafting component: vinyl or acrylic functional monomer/oligomer | 5–90% | |
| | 3. Photoinitiators | 0–10% | |
| | 4. Solvents | N/A | 40–99% |
| Top coat | 1. Therapeutic, diagnostic, or hydrophilic agent: amine containing compound. | | 0.01–20% |
| | 2. Solvents | | 80–99.9% |

EXAMPLE 2

Device Coated with a Base Coat and a Hydrophilic Top Coat of Formula I

A base coat comprising 0.5 grams (gm) tri-aziridine oligomer (Zeneca cx-100), 1.5 gm trimethylol propane tri-acrylate, with an intermediate chain extension of 200 molecular weight (mol. wgt.) PEG (Henkel Photomer 4158), 0.004 gm benzophenone and 0.004 gm. 2,2 dimethoxy-2-phenylacetophenone, in 17.9 gm n-butyl acetate was applied to a coronary dilatation catheter that had been chemically cleaned and plasma treated by dip coating the catheter in a base coat solution at 20 inches per minute. The base coated device was dried for 20 seconds at 110° F., then irradiated in front of a Fusion Systems, "H" Bulb, ultra-violet source for 20 seconds at a minimum intensity of 50 milliwatts per square centimeter. A top coat of 1.5 gm poly(acrylic acid) (mol. wgt. 250K), 99 gm water, 25 gm 2-propanol, and 0.5 gm 28% $NH_3$ to increase acrylic acid solubility, was then applied by dip coating the base coated device in a top coat solution at 20 inches per minute. The coated device was then dried in a convection oven at 55° C. for 15 minutes. The dried coated device was then dipped in 0.1 N KOH, and rinsed freely with water, to neutralize any free carboxyl groups on the hydrophilic polymer to increase the hydrophilic character of the topcoat and enhance its lubricity. The resulting catheter having a lubricious hydrophilic coating is extremely lubricious when wet, and the coating showed resistance to wearing off. If rubbed repeatedly under running water and then tested for lubricity against an excised porcine aorta counter surface, the catheter had a coefficient of friction of 0.08. A similar unit without the basecoat of the invention had a coefficient of friction of 0.32, which is equivalent to an uncoated catheter.

EXAMPLE 3

Device Coated with a Base Coat and a Hydrophilic Top Coat of Formula II/III

The procedure outlined above in Example 2 was performed using lubricious hydrophilic coatings from the class of coatings labeled "Formula II" and "Formula III" in Example 1, except that the dried coated device is not dipped in a basic neutralizing solution. Thus, the base coat was applied to a coronary dilatation catheter that was chemically cleaned and plasma treated, by dip coating at 20 inches/min. The base coated catheter was then dried for 20 seconds at 110° F., and then irradiated in front of an ultra-violet source (Fusion Systems, "H" Bulb) for 20–90 sec. at a minimum intensity of 50 milliwatts per square centimeter. The top coat was then applied by dip coating at 20 in./min., and the coated catheter was baked in a convection oven at 55° C. for 15 min. The resulting catheter having a lubricious hydrophilic coating is extremely lubricious when wet, and the coating showed resistance to wearing off.

The specific coatings used were as follows:

For Formula II, the base coat was 1.5 gm isocyanurate trimer of 1,6 hexamethylene diisocyanate (Bayer Desmodur N-3300), 0.5 gm trimethylol propane tri-acrylate, with an intermediate chain extension of 200 mol. wgt. PEG (Henkel Photomer 4158), 0.004 gm benzophenone, 0.004 gm 2,2 dimethoxy-2-phenylacetophenone, 0.0005 gm dibutyl tin dilaurate, and 17.9 gm n-butyl acetate, and the top coat was 2.0 gm poly(vinyl alcohol) (mol. wgt. 100K), and 98.0 gm water.

For Formula III, the base coat was 2.0 gm of glutaraldehyde (25% in water), 1.5 gm trimethylol propane tri-acrylate, with an intermediate chain extension of 200 mol. wgt. PEG (Henkel Photomer 4158), 0.004 gm benzophenone, 0.004 gm 2,2 dimethoxy-2-phenylacetophenone, and 17.9 gm 2-propanol, and the top coat was 2.0 gm gelatin (175 bloom, swine skin, Aldrich Chemical Co.), and 98.0 gm water.

EXAMPLE 4

Device Coated with a Base Coat and a Therapeutic or Diagnostic Top Coat of Formula II/III A base coat comprising 12.25 grams (gm) difunctional urethane-acrylate (Henkel 12-892), 1.0 gm hydroxycyclohexylphenyl ketone (Aldrich), 1.0 gm benzophenone (Aldrich), 2.45 gm cellulose acetate butyrate (Acros), 180 gm ethyl acetate (Aldrich), and either 12.25 gm cinnamaldehyde (Aldrich) (Formula III) or 12.25 gm a,a-Dimethyl meta-isopropenyl benzyl isocyanate (i.e., TMXDI) (Cytec) (Formula II), was applied to a stent that had been sonicated in a clean IPA for 1 minute, by dip coating. The stent was extracted form the base coat solution at a rate of 10 inches per minute, and was irradiated in front of a medium pressure Mercury lamp at an intensity of 10–15 milliwatts per square centimeter, for 8 minutes. A top coat of 1.0% peptide, such as albumin, solution was then applied by immersion of the based coated stent in a top coat solution for 2 hours at 50° C. The coated stent was then removed and baked for 10 minutes at 50° C. The dried, coated stent was then soaked in distilled water for 20 minutes at 50° C., and baked until dry.

EXAMPLE 5

Formula for Lubricious Hydrophilic Coating Having a Blend of a Grafting Component and a Hydrophilic Top Coat

| Component | % of Non-Volatile | % of Total Formula |
| --- | --- | --- |
| 1. Grafting component: vinyl or acrylic functional monomer/oligomer | 5–45% | |
| 2. Hydrophilic compound | 50–95% | |
| 3. Salt | 0.1–40% | |
| 4. Photoinitiators | 0.0–10% | |
| 5. Solvents | N/A | 80–99.9% |

1.36 gm of trimethylol propane triacrylate with an intermediate chain extension of 200 mol. wgt. PEG(Henkel Photomer 4158), 0.018 gm benzophenone and 0.018 gm 2,2 dimethoxy-2-phenylacetophenone were dissolved in 30 gms 2-propanol. The solution was then added to 653 gm 2-propanol in a container equipped with a stirrer. With agitation, 7.5 gms poly(ethylene oxide), 1 million mol. wgt, was added. 1.5 gms potassium bromide was dissolved in 116 gms water, and added to above. This solution was stirred until poly(ethylene oxide) was fully dissolved, about 1 hour.

The coating was applied to a coronary dilatation catheter that was chemically cleaned and plasma treated, by dip coating at 20 in./min. The coated catheter was dried for 20 sec. at 110° F., and then UV irradiate as outlined above. When evaluated in a friction test using excised porcine aorta as a countersurface, the hydrophilic coating yields an average force of 31 gm, as opposed to 98 gm for a control silicone coating, for a 68% reduction in force.

EXAMPLE 6

Formula for Primer Coating and Lubricious Hydrophilic Coatings for Coating A Metal Device

| Coating Layer | Component | % of Non-Volatile | % of Total Formula |
| --- | --- | --- | --- |
| Primer coat | 1. Vinyl or acrylate containing monomer or oligomer | 90–100% | |
| | 2. Photoinitiators | 0–10% | |
| | 3. Solvents | N/A | 60–99% |
| Hydrophilic coating blend | 1. Grafting component: vinyl or acrylic functional monomer/oligomer | 5–49% | |
| | 2. Hydrophilic compound | 50–95% | |
| | 3. Salt | 0.1–40% | |
| | 4. Photoinitiators | 0.0–10% | |
| | 5. Solvents | N/A | 80–99.9% |

In 100 gm of ethyl acetate, was dissolved 0.05 gm benzophenone, 0.05 gm 2,2 dimethoxy-2-phenylacetophenone, and 20 gm bisphenol A ethoxylate diacrylate (Henkel Photomer 4028). The primer was applied to a chemically cleaned guidewire by dip coating at 20 in/min, and dried for 15 sec. at 100° F., and irradiated with UV source (Fusion Systems, "H", Bulb) for 25 sec. at minimum intensity of 50 milliwatts/cm$^2$. For the hydrophilic coating, 0.84 gm trimethylol propane triacrylate, 0.018 gm benzophenone and 0.018 gm 2,2 dimethoxy-2-phenylacetophenone was dissolved in 30 gms 2-propanol. It was added to 650 gm 2-propanol in a container equipped with a stirrer. With agitation, 7.5 gms poly(ethylene oxide), 1 million mol. wgt, was added. 0.4 gm potassium bromide was dissolved in 116 gms water and added to above. The mixture was stirred until poly(ethylene oxide) was fully dissolved, about 1 hour. The top coat was applied to the primed guidewire by dipping, drying, and then irradiating as outlined for the primer coat.

The guidewire thus coated has a durable lubricious coating when wet, resulting in a coefficient of friction of 0.03, compared to a coefficient of friction of 0.18 for a silicone coating. The hydrophilic coating was found to slough off rapidly when wet if the primer coat was omitted.

Although the invention has been described herein in terms of certain preferred embodiments, modifications and improvements thereof may be made without departing from the scope of the invention.

What is claimed is:

1. A method of coating an intracorporeal medical device, comprising:

a) applying to the medical device a solution having a grafting component and a binding component, wherein the grafting component is selected from the group consisting of vinyl, acrylate and allyl compounds, and the binding component has at least a first functional group selected from the group consisting of aziridine, carbodiimide, aldehyde, isocyanate, succinimide, maleimide, oxirane, and carboxyl derivatized with one of carbodiimide, tresyl, or succinimide;

b) polymerizing the grafting component in the presence of the binding component, so that the grafting component polymerizes on the medical device, and bonding the grafting component to the binding component, to form a base coat on the device; and c) applying to the base coat a top coat having a functional group which binds to the binding component.

2. The method of claim 1 wherein the top coat comprises a therapeutic, diagnostic, or hydrophilic agent having said functional group of the top coat, and wherein applying the top coat to the base coat comprises covalently bonding the functional group of the therapeutic, diagnostic or hydrophilic agent to the functional group of the binding component.

3. The method of claim 2 wherein the therapeutic, diagnostic, or hydrophilic agent functional group is selected from the group consisting of carboxyl, hydroxy, amine, and thiol, and applying the top coat to the base coat comprises applying a solution of the therapeutic, diagnostic or hydrophilic agent to the base coat and drying the coated medical device after the solution of the therapeutic, diagnostic or hydrophilic agent is applied to the base coat.

4. The method of claim 1 wherein the top coat comprises a linking agent having said functional group of the top coat, the linking agent functional group being selected from the group consisting of carboxyl, hydroxy, amine, and thiol, and including exposing the linking agent to a therapeutic, diagnostic or hydrophilic agent so that a complex comprising the therapeutic, diagnostic, or hydrophilic agent and the linking agent is formed.

5. The method of claim 1 wherein the binding component is a homofunctional compound having a first functional group selected from the group consisting of trifunctional isocyanate, carbodiimide, trifunctional aziridine, and difunctional aldehyde and bonding the grafting component to the binding component comprises covalently bonding the binding component to the grafting component.

6. The method of claim 1 wherein the binding component is a heterofunctional compound containing the first functional group for bonding to the top coat and a second functional group for covalently bonding with the grafting component, the second functional group being selected from the group consisting of methacrylate, acrylate, vinyl, and allyl, and bonding the grafting component to the binding component comprises copolymerizing the binding component with the grafting component.

7. The method of claim 1 wherein the top coat comprises a first linking agent having said functional group of the top coat, the linking agent functional group being selected from the group consisting of carboxyl, hydroxy, amine, and thiol, and a second linking agent bound to the first linking agent, and including exposing the second linking agent to a therapeutic, diagnostic or hydrophilic agent so that a complex comprising the therapeutic, diagnostic, or hydrophilic agent and the second linking agent is formed.

8. The method of claim 4 wherein the linking agent is selected from the group consisting of functionalized liposomes, microsponges, and microspheres, and including covalently bonding the functional group of the liposome, microsponge, or microsphere to the binding component.

9. The method of claim 4 wherein the linking agent comprises an avidin-biotin complex having an avidin moiety bound to a biotin moiety, and including covalently bonding an amine or a carboxyl functional group of the biotin moiety or the avidin moiety to the binding component.

10. The method of claim 1 wherein the medical device has a polymeric surface or coating, and step b includes covalently bonding the grafting component to the polymeric surface or coating.

11. The method of claim 3 including hydrating the hydrophilic agent on the medical device to form a lubricious hydrophilic coating.

12. The method of claim 1 wherein the binding component is selected from the group consisting of polyaziridine and polycarbodiimide resin compounds when the top coat functional groups are carboxyl groups, and including exposing the top coat on the medical device to a basic solution, so that free carboxyl groups on the top coat are neutralized.

13. The method of claim 1 wherein applying the top coat comprises applying a solution of the top coat, and including drying the coated medical device after at least one of the solutions of the grafting and binding components or the top coat are applied to the medical device.

14. The method of claim 1 wherein polymerizing the grafting component comprises irradiating the grafting component with ultra-violet radiation.

15. The method of claim 1 wherein polymerizing the grafting component comprises irradiating the grafting component with electron beam radiation.

16. A method of providing a therapeutic, diagnostic or hydrophilic coating on an intracorporeal medical device, comprising:
   a) applying to the medical device a solution having a grafting component and a binding component, wherein the grafting component is selected from the group consisting of vinyl, acrylate and allyl compounds, and the binding component has at least a first functional group selected from the group consisting of aziridine, carbodiimide, aldehyde, isocyanate, succinimide, maleimide, oxirane, and carboxyl derivatized with one of carbodiimide, tresyl, or succinimide;
   b) polymerizing the grafting component in the presence of the binding component, so that the grafting component polymerizes on the medical device, and bonding the grafting component to the binding component, to form a base coat on the device; and
   c) applying to the base coat a solution of a therapeutic, diagnostic or hydrophilic agent having a functional group which covalently bonds to the binding component, to form the therapeutic, diagnostic or hydrophilic coating on the medical device.

17. A method of providing a therapeutic, diagnostic or hydrophilic coating on an intracorporeal medical device, comprising:
   a) applying to the medical device a solution having a grafting component and a binding component, wherein the grafting component is selected from the group consisting of vinyl, acrylate and allyl compounds, and the binding component has at least a first functional group selected from the group consisting of aziridine, carbodiimide, aldehyde, isocyanate, succinimide, maleimide, oxirane, and carboxyl derivatized with one of carbodiimide, tresyl, or succinimide;
   b) polymerizing the grafting component in the presence of the binding component, so that the grafting component polymerizes on the medical device, and bonding the graft component to the binding component, to form a base coat on the device;
   c) applying to the base coat a solution comprising a linking agent having a functional group which covalently bonds to the binding component; and
   d) exposing the linking agent to a solution of a therapeutic, diagnostic or hydrophilic agent, so that a complex comprising the linking agent and the therapeutic, diagnostic or hydrophilic agent is formed, to form the therapeutic, diagnostic or hydrophilic coating on the medical device.

* * * * *